(12) United States Patent
Lynch et al.

(10) Patent No.: US 7,172,426 B1
(45) Date of Patent: Feb. 6, 2007

(54) USE OF OZONE FOR THE TREATMENT OF MOUTH ULCERATIONS

(75) Inventors: Edward Lynch, Belfast (GB); Jurgen Schemmer, King City (CA)

(73) Assignee: Curozone Ireland Limited, Dublin (IE)

( * ) Notice: Subject to any disclaimer, the term of this patent is extended or adjusted under 35 U.S.C. 154(b) by 80 days.

(21) Appl. No.: 10/999,088

(22) Filed: Nov. 29, 2004

Related U.S. Application Data

(62) Division of application No. 10/097,758, filed on Mar. 13, 2002, now Pat. No. 6,875,018.

(60) Provisional application No. 60/279,360, filed on Mar. 28, 2001.

(51) Int. Cl.
*A61C 5/02* (2006.01)

(52) U.S. Cl. .................. 433/224; 433/81; 433/224; 424/49; 424/613

(58) Field of Classification Search .................. None
See application file for complete search history.

(56) References Cited

U.S. PATENT DOCUMENTS

| 4,689,215 | A | * | 8/1987 | Ratcliff | 424/53 |
| 5,829,449 | A | * | 11/1998 | Hersh et al. | 131/202 |
| 6,135,126 | A | * | 10/2000 | Joshi | 132/308 |

* cited by examiner

*Primary Examiner*—Frederick Krass
*Assistant Examiner*—Lezah Roberts
(74) *Attorney, Agent, or Firm*—Walter A. Hackler

(57) ABSTRACT

A method of treating mouth ulcerations, includes directing a stream of oxidizing gas onto mouth ulcerations for a period of time sufficient to kill microorganisms.

2 Claims, 3 Drawing Sheets

USE OF OZONE FOR THE TREATMENT OF MOUTH ULCERATIONS

The present application is a division of U.S. Ser. No. 10/097,758 filed Mar. 13, 2002, now U.S. Pat. No. 6,875,018, which is a continuation of U.S. Ser. No. 60/279,360 filed Mar. 28, 2001. These applications are to be incorporated herewith by this specific reference thereto.

This invention relates to the use of ozone in he treatment of dental and oral conditions.

The great destructive disease of teeth is dental caries which may be defined as the acid dissolution of enamel, dentine or cementum as a consequence of the metabolism of micro-organisms living within deposits on the teeth known as plaque. Dental caries is believed to be associated with specific micro-organisms, the principal ones being *Streptococcus Mutans, Lactobacilli, Actinomyces* Visosus Serovar 2, *Actinomyces* Naesludii and "Intermediate" *Actinomyces*, other *Streptococci* and yeasts. These are acid producing micro-organisms which produce acids such as acetic and lactic acids from the dietary carbohydrates. The micro-organisms associated with dental caries are unique and are ecologically very different from those associated with, for example, infected root canals.

Dental caries is currently managed by one or more of the following:

(i) preventive treatment by, for example, dietary and oral hygiene measure and may include the topical application of chemotherapeutic agents;
(ii) the removal of dentine exhibiting the signs of active caries;
(iii) the protection of any newly exposed non-carious dentine with restorative material.

Measures aimed at the prevention or the arrest of dental caries are mainly based on the elimination of dental plaque from the surfaces of roots and the institution of dietary controls to reduce the frequency and quantity of readily fermentable carbohydrate ingestion. The mechanical removal of plaque has been a major platform for the prevention of dental caries for some time. However, this poses special problems in the case of primary root caries due to access problems. Because dentine has a Knoop hardness of 68 in contrast to enamel at 11, the mechanical removal of plaque from its surface inevitably results in some loss of tissue also. Toothbrush abrasion is now a very common phenomenon and invariably leads to the loss of root dentine from the facial aspects of teeth. Consequently, the traditional methods of plaque control in the prevention of dental caries create further problems even when access permits it to be used effectively.

Conventional caries removal and cavity preparation entail the use of high and low speed handpieces. However, disadvantages of this system include the perception that drilling is unpleasant for patients and local anesthetic is frequently required. Furthermore, handpieces are expensive to purchase and maintain and their use may lead to the removal of softened but uninfected dentine resulting in the excessive loss of tooth tissue.

Where restoration is required, all materials used to restore carious lesions have their limitations. For example, gold and ceramic are expensive and present a technical challenge for the practitioner. While amalgam is durable, predictable material, it has poor aesthetic qualities, is potentially toxic and may cause allergic reactions in some people.

It is an object of the invention to alleviate the disadvantages of the prior art.

It has now unexpectedly been found that ozone can penetrate carious tissue and can therefore be used in the treatment of dental caries.

According to the present invention there is provided the use of ozone in the preparation of a therapeutic system for the treatment of dental caries.

As used herein, the term "ozone" is intended to embrace pure ozone, oxonised air and ozonized aqueous media, such as water optionally containing a reductant, such as thiocyanate or peppermint.

The ozone is delivered at a pressure sufficient to penetrate the carious tissue and at a concentration and for a period of time sufficient to kill substantially all of the micro-organisms within the carious lesion.

Preferably, a needle-sized jet of pure ozone or ozonized air in a shroud of micro-organism-free aqueous medium, e.g. water optionally containing a reductant, is injected at the desired location.

If desired, a sealant of the type known in the art may be applied to a carious lesion following ozone treatment.

The advantages using ozone in the treatment of dental caries include the following:

1. It eliminates drilling and its attendant problems;
2. It is rapid and painless;
3. It does not require sophisticated methods of isolating the tooth;
4. No local anesthetic is required.

The invention is illustrated in the following Examples. Unless otherwise stated, the ozone delivered in the following Examples is present in air at a concentration of 5.2%,

EXAMPLE 1

Many studies concerning the clinical evaluation of ozone have been based on assessments of its harmful effects rather than demonstrating any therapeutic benefits it may offer. Ozone is one of nature's most powerful oxidants which accounts for its ability to kill bacteria, spores and viruses. Uniquely, ozone decomposes to a harmless, non-toxic and environmentally safe material (oxygen). In this investigation, a multicomponent evaluation of the oxidative consumption of salivary biomolecules by ozone ($O_3$) has been performed using high resolution proton ($^1H$) nuclear magnetic resonance (NMR) spectroscopy. The ozone-generating equipment employed in this study was designed by Purezone Ltd. (Ipswich, U.K.). Unstimulated human saliva samples were collected from 8 patients and each of them was divided into two equivalent portions (0.60 ml). The first of these was treated with $O_3$ generated from the above device for a period of 30 seconds; the second group of portions served as controls. Samples were subjected to $^1H$ NMR analysis at an operating frequency of 600 MHz. Results acquired revealed that $O_3$ treatment gave rise to (1) the oxidative decarboxylation of the salivary electron-donor pyruvate (generating acetate and $CO_2$, as products), (2) oxidation of the volatile sulphur compound precursor methionine to its corresponding sulphoxide and (3) the oxidative consumption of salivary polyunsaturated fatty acids. Moreover, evidence for the $O_3$-mediated oxidation of salivary 3-D-hydroxybutyrate was also obtained. High field $^1H$ NMR spectroscopy provides much useful analytical data regarding the fate of $O_3$ in human saliva, information which is of much relevance to its potential therapeutic actions in vivo.

EXAMPLE 2

Ozone Effect on Microflora from Primary Root Caries Ex-vivo

Primary root carious lesions (PRCL) are a major clinical problem. The aim of this study was to establish if ozone could achieve effective microbial killing in PRCL. An ozone producing generator (Purezone Ltd., Ipswich, U.K.) was used in this ex-vivo study assessing the use of ozone on PRCL. In this study, soft PRCL requiring restoration were used as these are the most severe type of lesion found in humans. 20 freshly extracted teeth with PRCL requiring restoration were used. After plaque removal using a hand held standard fine nylon fiber sterile toothbrush with sterile water as a lubricant to cleanse the surface, each tooth was then isolated using sterile cotton wool rolls and dried using a dry sterile cotton wool roll. A sample of PRCL was taken using a sterile excavator from half of the most active part of the lesion. Subsequently, 10 seconds of the ozonized water was applied to the lesion and another sample was taken from the other half of the most active part of the lesion. Each sample was weighed and immediately placed in 1 ml of Fastidious Anaerobe Broth (FAB). To each 1 ml of FAB containing a biopsy o carious or ozone treated carious dentine, sterile glass beads were added. They were vortexed for 30 seconds to facilitate the extraction of any micro-organisms from the carious dentine and disperse any aggregates. After decimal dilution with FAB, 100 ml aliquots of these was spread on Fastidious Anaerobe Agar (LabM, Bury, Lancs., U.K.) supplemented with 5% (V/V) horse blood in an anaerobic chamber at 37° C. for four days. The mean±SE number of each colony type was counted and calculated.

|  | Before Ozone Treatment | After 10 Seconds of Ozone Treatment |
|---|---|---|
| Mean ± SE of Total cfu ($Log_{10}$) | 5.9 ± 0.15 | 3.57 ± 0.37 |

Using the paired Student t-test a significant difference ($p<0.001$) was observed between the two groups. Clearly, the percentage of micro-organisms killed associated with the use of ozone was more than 99%.

EXAMPLE 3

Ozone Effect on Microflora from Primary Root Caries Ex-vivo

The procedure of Example 2 was repeated except that ozonized water was applied to the lesion for 20 seconds. Using the paired student t-test, a significant difference was observed in the ozonized water group ($log_{10}$ 3.77±0.42, mean±SE) compared with the control group ($log_{10}$ 6.18±0.21) ($p<0.001$).

The results of these tests show that the use of ozone can provide an effective, rapid and simple means for killing micro-organisms in carious lesions.

EXAMPLE 4

Sealant Shear Bond Strength to Sound and Carious Radicular Dentine

These has been little research on the interaction between primary root carious lesions (PRCL) and adhesive materials. The aim of this study was to examine the shear bond strength of four adhesive systems to PRCL with sound dentine acting as a control. The adhesive systems used were:

1. OptiBond FL Prime[1]/OptiBond FL Adhesive[1]/OptiGuard[1]
2. OptiBond FL Prime/OptiGuard
3. OptiGuard and
4. ChemFil II[2]

[1]Kerr, Romulus, Mich., U.S.A.;
[2]Dentsply, Konstanz, Germany.

The materials were applied to sound radicular dentine and PRCL in vitro in freshly extracted teeth. The bonding site was macroscopically intact, was flat and had at least a 3.5 mm diameter. 37% phosphoric acid was used for 15 seconds in samples in groups 1->3 whilst 25% polyacrylic acid was used in group 4. After bonding the samples were stored for seven days in a moist atmosphere at 37° C. A shearing force was applied at 1 mm/minute. There were at least 10 samples in each group. The mean (s.e.) shear bond strengths were (MPa);

| Adhesive | Control | Carious |
|---|---|---|
| OptiBond FL Prime/Optibond FL Adhesive/OptiGuard | 5.31 (1.03) | 5.58 (1.05) |
| Optibond FL Prime/OptiGuard | 2.01 (0.59) | 1.63 (0.40) |
| OptiGuard | 0.73 (0.24) | 1.45 (0.52) |
| ChemFil II | 1.42 (0.28) | 1.01 (0.26) |

While statistical testing showed that the shear bond strength of the OptiBond FL Prime/OptiBond FL Adhesive/OptiGuard was significantly the highest, ($p<0.001$), the caries status of the root surface had no significant influence on the bond strength. OptiGuard in combination with OptiBond FL Prime and OptiBond Adhesive had the highest bond strength and this was not influenced by the caries status of the surface.

EXAMPLE 5

The effect of ozone on primary root caries and associated micro-organisms

The aims of these studies were to evaluate the efficiency of ozone on primary root caries and associated micro-organisms (*Streptococcus sobrinus*; TH 21 *Streptococcus mutans*; NCTC 10449). In study 1, 40 soft primary root carious lesions (PRCLs) from freshly extracted teeth were used and randomly divided into two groups to test the exposure to ozone for either 10 or 20 seconds. There was a significant ($p<0.001$) difference (Mean±SE) between the control samples for either 10 seconds ($log_{10}$ 5.91±0.15) or 20 seconds ($log_{10}$ 6.18±0.21) and ozone treated samples for either 10 seconds ($log_{10}$ 3.57±0.37) or 20 seconds ($log_{10}$ 3.77±0.42). In study 2, 40 sterile saliva coated glass beads were put into bijoux bottles with 3 mls of Todd Hewitt broth for control and test groups. *S. sobrinus* and *S. mutans* were inoculated and incubated anaerobically overnight. Each glass bead was washed with 2 mls of PBS. Immediately, 10 seconds of ozone was applied to the glass beads in the test-groups. Subsequently, each glass bead in the test and control groups was placed in 3 mls of Todd Hewitt broth with six more sterile glass beads and were vortexed for 30 seconds. After decimal dilutions, 100 ml aliquots were spread on blood agar plates supplemented with 5% (V/V) horse blood and placed in an anaerobic chamber at 37° C. for two days. The number of each colony type was counted and calculated. Using the paired student t-test, there was a significant reduction (p<0.0001) (Mean±SE) between the control samples for *S. sobrinus* ($\log_{10}$ 4.61±0.13) and *S. mutans* ($\log_{10}$ 3.93±0.07) and ozone treated samples for *S. sobrinus* ($\log_{10}$ 1.09±0.36). This treatment regime is therefore an effective, quick, conservative and simple method to kill micro-organisms in primary root carious lesions.

EXAMPLE 6

The effect of ozone on gum disease.

Inflamed human gingivitis is exposed to ozone using the techniques herein described. After exposure to ozone, the inflammation is illuminated or reduced. In addition, enzyme levels in extracts from inflamed human gingiva are alleviated and/or reduced.

EXAMPLE 7

The effect of ozone on the treatment of root canals.

Bacteria cultures of *Streptococcus aurous, Lactobacillus salivarius* and *Lactobacillus acidophilus*, known as being associated with dental diseases are exposed to ozone using the techniques herein described and growth of the bacteria cultures is eliminated or inhibited.

EXAMPLE 8

The effect of ozone in the treatment of month ulcerations.

Month ulcerations are exposed to ozone using the techniques herein described and microorganisms in the ulceration are eliminated or reduced. In addition, enzyme levels in the month ulcerations are alleviated and/or reduced.

EXAMPLE 9

The effect of ozone in the treatment of bad breath.

Bad breath is caused, in part, by the retention and subsequent degradation of dead cellular material, by microorganisms, sloughed off continuously by a normal, healthy mouth. A mouth is exposed to ozone using the techniques herein described and the microorganisms associated with bad breath are eliminated or reduced. In addition enzyme levels in the month are alleviated and/or reduced.

The present invention further relates to apparatus for the treatment of dental caries utilizing an oxidizing gas.

The role of specific micro-organism such as, for example, *streptococcus* mutants in dental caries is well documented. Enzymes produced by such micro-organisms synthesize dextran from the sucrose passing through the month with food or drink resulting in the formation of dental plaque and dental caries.

Dental caries is the decay of teeth caused by demineralization of the enamel surface with organic acids produced by bacteria which adhere to teeth surfaces.

Heretofore, dental caries have been removed through the use of conventional grinding handpieces, lasers and air-blasting apparatus. However high-speed turbine drills or low-speed drills unfortunately will grind both caries and sound dentine. Accordingly, a practitioner must select and grind only caries and consequently, this method depends upon this skill of the practitioner. Lasers have been utilized to remove caries, however, not much success has been achieved for varies reasons. For example, blackened charred tissue blocks the laser radiation which, in turn, prevents the laser from reaching caries therebelow. In addition, heating also interrupts the ablation process.

With regard to air-blasting treatment of caries sound, dentine may also be easily removed, and accordingly, the skill of the practitioner is of outmost importance.

The present invention provides for the treatment of caries without the disadvantages of the prior art hereinabove noted.

SUMMARY OF THE INVENTION

Apparatus for the treatment of dental caries in accordance with the present invention generally includes a source of oxidizing gas and a handpiece for delivering the gas to a tooth. A cup attached to the handpiece, is provided for receiving the gas and exposing a selected area of the tooth to the gas.

The cup may include a resilient edge for sealably engaging the tooth around the selected area to prevent escape of the gas therepast. Alternatively, a suitable sealant may be utilized for providing the sealed engagement between the cup and the tooth. This enables a totally closed system for the application of the gas to the tooth.

A source of oxidizing gas may include an ozone generator and an ozone pump. An aspiration pump may be provided, along with an aspiration line connected to the handpiece, for enabling circulation of the gas into and out of a cup chamber subtending the cup edge. In that regard a controller may be provided for regulating the ozone and aspiration pumps in order to circulate the gas into an out of the cup chamber at a pressure insufficient to escape past the sealed engagement between and the tooth.

The apparatus may further include a source of reductant, in fluid communication with the cup chamber and a reductant pump may be provided for circulating the reductant through the cup chamber in order to flush the oxidizing gas from the cup chamber and into the aspiration line.

A waste accumulator may be provided and connected to the aspiration line for receiving the reductant. In addition, a filter may be provided for removal of any residual oxidizing gas from the aspiration line.

In one embodiment of the present invention the cup edge includes a relatively uniform perimeter for sealably engaging a tooth between a cusp and a gingiva. In another embodiment of the present invention, a cup edge may include a contour enabling a sealably engagement with adjacent teeth. More specifically, the cupped edge may have a perimeter contoured for sealably engaging cusps of adjacent teeth.

BRIEF DESCRIPTION OF THE DRAWINGS

The advantages and features of the present invention will be better understood by the following description when considered in conjunction of the accompanying drawings, in which.

DETAILED DESCRIPTION

Figure 1:
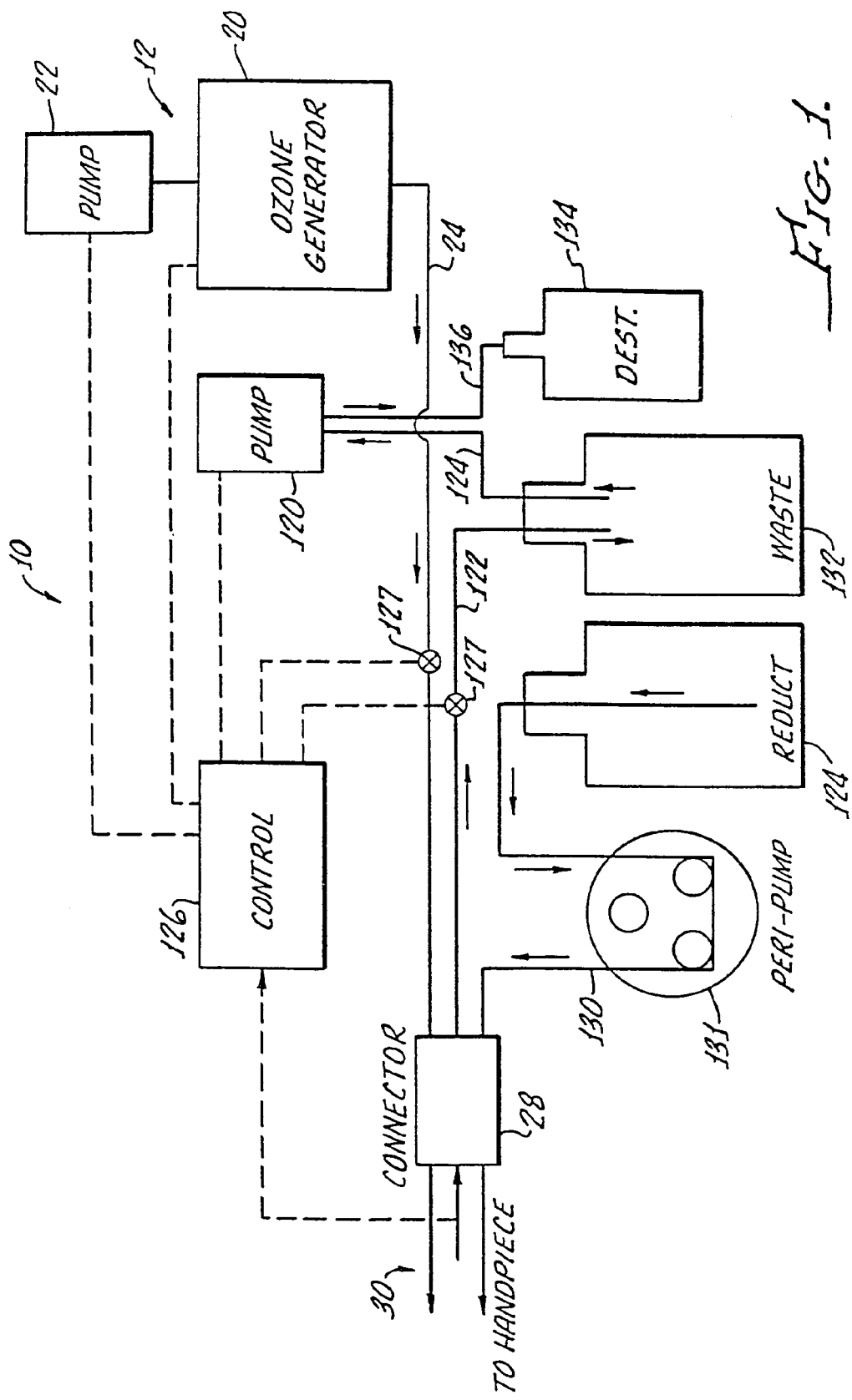
FIG. 1 illustrates a block diagram of apparatus for treatment of dental caries in accordance with the present invention, the apparatus generally includes a source of oxidizing gas, an aspiration pump, a source of reductant, a reductant pump and a controller for providing the oxidizing gas to a handpiece.
Figure 2:
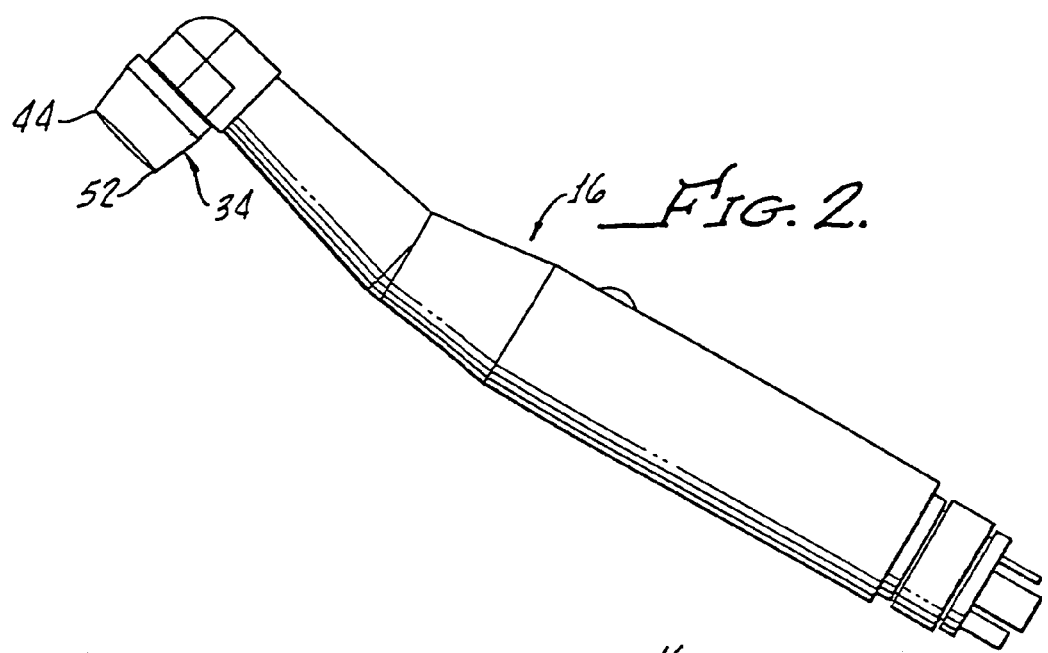
FIG. 2 illustrated a handpiece in accordance with the present invention for delivering a gas to a tooth and generally showing a cup attached to the handpiece for receiving the gas.
Figure 3:
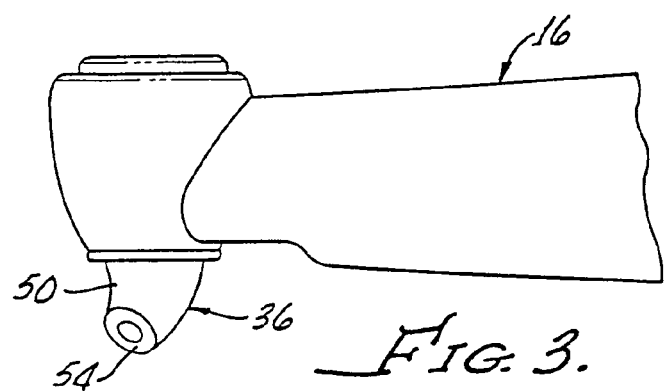
FIG. 3 illustrated the handpiece with an alternative cup embodiment, the alternative embodiment cup having an arcuate shape for facilitating application of oxidizing gas to a tooth.

With reference to FIGS. 1–4, there is shown apparatus 10 in accordance with the present invention for the treatment of dental caries which includes a source 12 of oxidizing gas, preferably ozone, and a handpiece 16 (see FIG. 2) for delivering the gas to a tooth, not shown in FIGS. 1–3. The effectiveness of an oxidizing gas such as ozone is set forth in co-pending International Patent Application PCT/EP99/04035 now U.S. Ser. No. 09/700,275 entitled "Use Of Ozone For The Preparation Of Medicaments For The Treatment of Dental Caries" by Edward Lynch. This application is incorporated herewith in its entirety including all specification and drawings by this specific reference thereto.

As illustrated in FIG. 1, the ozone source 12 includes an ozone generator 20 and an ozone pump 22 for supplying ozone through a line 24, a connector 28 and lines 30 to the handpiece 16. As used herein, the term "ozone" is intended to embrace any suitable oxidizing gas, pure ozone, ionized air and other ozone gaseous mixtures.

As noted in the referenced international patent application, ozone is delivered at a pressure, concentration and for a period of time sufficient to penetrate the carious tissue and kill substantial all of the micro-organism within a carious lesion. Specific examples of the use of ozone are set forth in the referenced patent application and are incorporated herewith by the specific reference thereto.

As shown in FIGS. 2–3, cups 34 36 attached to the handpiece 16 are provided for receiving the gas and exposing a selected area 38 on a tooth 40, see FIG. 3. The cup 34 may be attached to the handpiece 16 in any conventional manner and include a resilient edge, or sidewall, 44 for sealable engaging the tooth 40 to prevent the escape of gas therepast.

Figure 4:
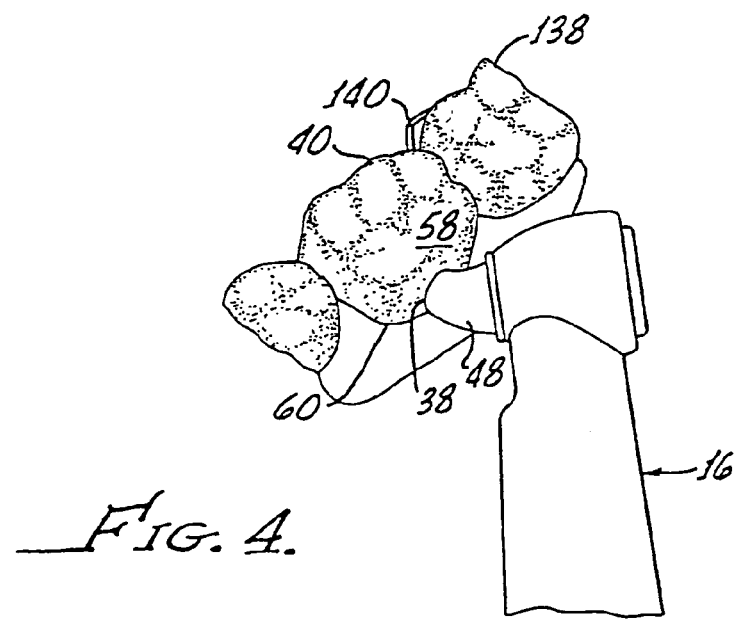
FIG. 4 is a diagram showing application of oxidizing gas to a tooth between a cusp and a gingival utilizing the handpiece and cup shown in FIG. 3.

Many different sized and shaped cups may be utilized, as for example shown in FIG. 3 the cup 36 includes an arcuate trunk 50 to facilitate the placement of the cup 36 over the selected area 38 as shown in FIG. 4. The cups 34, 36 may have relatively uniform perimeters 52, 54 for sealably engaging the tooth 40 between a cusp 58 and a gingiva 60 as shown in FIG. 4.

Figure 6:
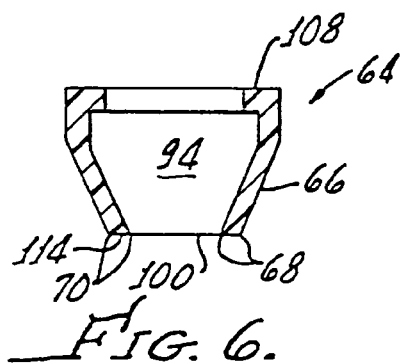
FIG. 6 is a cross sectional view an alternative embodiment of a cup for exposing a selected area of a tooth oxidizing gas.

A further cup embodiment 64 is shown in cross-section in FIG. 6 includes a tapered sidewall 66 that may be used for application of oxidizing gas to a smaller selected area (not shown) on the tooth 40.

While a resilient edge or sidewall may be used to couple the cup to the selected area 38 on the tooth 40, it should be appreciated that a separate sealant 68 (See FIG. 6) may be utilized for providing a sealable engagement between the cup 64 and the tooth 40. In this instance, the sidewall 66 need not be resilient.

Figure 7:
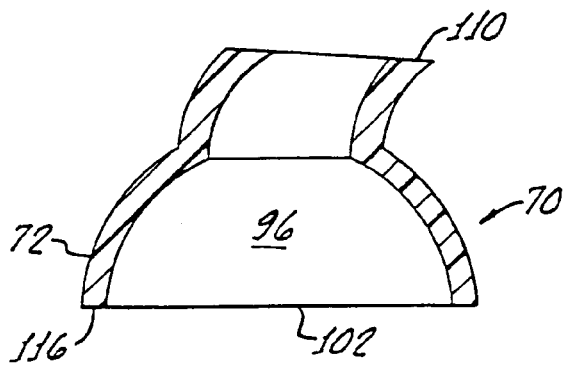
FIG. 7 is a cross sectional diagram showing an alternative embodiment of a cup in accordance with the present invention for exposing adjacent teeth to oxidizing gas.
Figure 8:
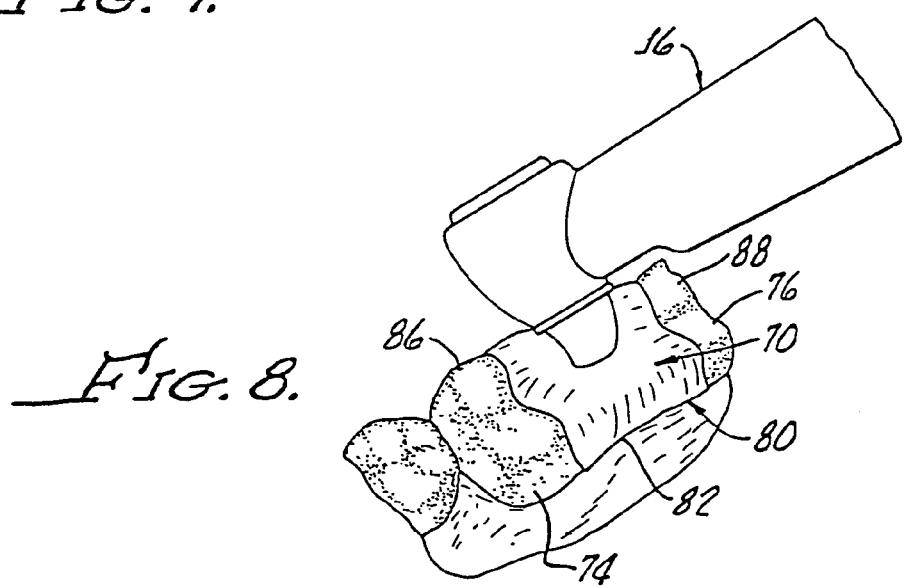
FIG. 8 illustrates the use of the cup shown in FIG. 7 as it may be applied to adjacent teeth.

Another embodiment of a cup 70 is shown in cross-section in FIG. 7 which includes walls 72 which are contoured for enabling the sealable engagement with adjacent teeth 74, 76 as shown in FIG. 8. As shown in FIG. 8, a cup edge 80 has a perimeter contour 82 for providing a sealable engagement with cups 86, 88 of adjacent teeth 74, 76.

Figure 5:
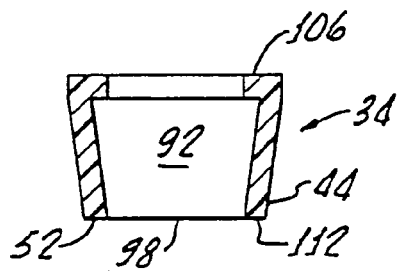
FIG. 5 is cross-sectional view of the cup shown in FIG. 2 that is suitable for use in the present invention.

All of the cups 34, 64, 70, cross-sectionally illustrated in FIGS. 5–7. include cup chambers 92, 94, 96 that subtend cup edges 98, 100, 102. As shown each of the cups 34, 64, 70 include walls 44, 66, 72 that define the chambers 92, 94, 96 and include first perimeters 106, 108, 110 for sealably coupling the walls 44, 66, 72 to the handpiece 16. Second perimeters 112, 114, 116 provide for coupling the walls 44, 66 72 to the tooth 40 and exposing the selected areas 38 to gas circulated in the chambers 92, 94, 96.

As shown in FIG. 6, the embodiment 64 the first perimeter 108 may be larger than the second perimeter 115 or, as shown in FIG. 7, the first perimeter 110 may be smaller than the second perimeter 116. Accordingly this variation in cup 64, 70 design enables the application of oxidizing gas the any number of tooth contours and to the application of oxidizing gas to a plurality of teeth has hereinabove described.

With reference again to FIG. 1, the apparatus 12 includes an aspiration pump 120 and lines 30, 122, 124 connected to the handpiece 16 for enabling circulation of the ozone into and out of the cup chambers 92, 94, 96.

A controller 126, which may be of any conventional circuit design, is provided for regulating the ozone and aspiration pumps 22, 120 in order to circulate the gas into and out of the cup chambers 92, 94, 96 at a pressure insufficient to permit escape of the gas past a sealed engagement between the cups 34, 64, 70 and teeth 40, 86, 88. Control of the gas flows may also be effected through valves 127, 127 regulated by the controller 126.

Additionally, the apparatus 10 may include a reductant source 128, which is in fluid communication with the cup chambers 92, 94, 96 through lines 30, 130 and a parastalic pump 131. The reductant, which may be a solution of thiocyanate or peppermint, is utilized to flush the cup chambers 92, 94, 96 of oxidizing gas. The oxidizing gas is flushed into the aspiration line 122 following ozone treatment of the tooth 40, 86, 88. The reductant is then aspirated through line 122 and into a waste accumulator 132.

Any residual ozone is then aspirated from the accumulator 132 through the line 124 and into a canister 134 through line 136 for final elimination of the ozone. Thus, the apparatus 12 provides for a totally closed system for the application and removal of ozone to and from teeth 40, 86, 88.

It should also be appreciate that when the cups 34, 36, 64 are utilized between teeth 40, 138 (not shown in FIG. 4) a separate dam 140 maybe utilized as necessary to enable the cups 34, 36, 64 (not shown in FIG. 4) to sealably enclose a selected area for treatment between the teeth 40, 138.

EXAMPLE 1

Ozone detection (ppm) around the cup using a ozone analyzer after either 10 or 20 s of ozone application in vivo Study or Test: Ozone detection (ppm) around the cup 34 using a ozone analyzer after either 10 or 20 s of ozone application in vivo Purpose: To assess the maximum ozone detectable level (ppm) around the cup 34 after either 10 s or 20 s of ozone application in vivo.

Study or Test Protocol: 20 primary root carious lesions (PRCLs) were randomly selected when the cross-sectional study was conducted. The tip of the sensor was always held within 2 mm of the edge of the cup, positioned half way between the mesial and occlusal sides of the cup. The maximum ozone detectable level (ppm) around the cup from the extracted teeth using an ozone analyzer after 10 s of ozone application. The ozone analyzer used was an API 450 model available from ENVIRO Technologies, UK, and was calibrated by the supplier within the previous week of delivery and this device was not used for any other purpose other than this study in the interim.

Overlying plaque was then removed using a hand held standard fine nylon fiber sterile toothbrush with water as a lubricant. Each tooth was dried using dry sterile cotton wool rolls and a dental 3 in 1-air syringe. The excavator blade was used to traverse the lesion in line with long axis of the tooth across the maximum gingival/occlusal dimension. Half of each lesion was removed using a sterile excavator. Subsequently, the remaining lesion was exposed to the ozone gas for a period of either 10 s or 20 s at room temperature (23° C.) and maximum detectable ozone level was also measured using this ozone analyzer.

Test Results:

The maximum ozone detectable level (ppm) around the cup from lesions for a period of either 10 s (Table 1 and FIG. 1) or 20 s (Table 2 and FIG. 2) ozone application during the treatment of root carious lesions were as follows:

TABLE 1

Maximum ozone detectable level (ppm) after a 10 s of ozone application

| Teeth types | Sites | Ozone detection (10 s) |
| --- | --- | --- |
| Upper left incisor | Mesial | 0.066 |
| Upper right 1. premolar | Buccal | 0.001 |
| Upper right canine | Distal | 0.002 |
| Upper right 1. molar | Buccal | 0.006 |
| Upper left 2. premolar | Buccal | 0.076 |
| Lower right 2. premolar | Mesial | 0.058 |
| Lower left 1. premolar | Buccal | 0.169 |
| Lower left lateral | Buccal | 0.106 |
| Upper right lateral | Distal | 0.001 |
| Lower left canine | Labial | 0.147 |

TABLE 2

Maximum ozone detectable level (ppm) after a 20 s of ozone application

| Teeth types | Sites | Ozone detection (20 s) |
| --- | --- | --- |
| Lower left lateral | Labial | 0.137 |
| Lower left 1. premolar | Buccal | 0.177 |
| Lower right incisor | Labial | 0.069 |
| Upper right canine | Labial | 0.033 |
| Upper right lateral | Labial | 0.079 |
| Lower left 2. premolar | Buccal | 0.002 |
| Lower right 1. molar | Buccal | 0.083 |
| Upper left lateral | Labial | 0.004 |
| Lower left canine | Labial | 0.056 |
| Upper left 1. premolar | Mesial | 0.001 |

Conclusion: The use of a cup is a safe way of delivering ozone when ozone was applied for a period of either 10 s or 20 s on the root carious lesions.

EXAMPLE 2

Assessment of Maximum Ozone Levels from Extracted Teeth after the use of Ozone for 10 s.—An In Vitro Test Report Study or Test: Assessment of the maximum detectable ozone levels, detected adjacent to the cup, from extracted teeth after the use of ozone for 10 s in vitro.

Purpose: To assess the maximum ozone detectable level (ppm) around a cup from the extracted teeth after a 10 s application of ozone.

1. Study or Test Protocol: 14 extracted teeth were selected. The tip of the sensor was always held within 2 mm of the edge of the cup, positioned half way between the mesial and occlusal sides of the cup. The maximum ozone detectable level (ppm) around the cup from the extracted teeth using an ozone analyzer was recorded during 10 s of ozone application with the generator setting on maximum at level 10. The ozone analyzer used was the API 450 model and this was calibrated by the supplier within the previous week of delivery. This device was not used for any other purpose other than this study in the interim.

The Ozone Delivery System

After plaque removal with 2 sterile cotton wool rolls, ozone gas was delivered onto the surface of each primary root carious lesion in each extracted tooth for 10 s after the lesion was dried for three seconds with a standard three in one dental syringe.

Test Results:

The maximum ozone detectable level (ppm) around the cup from the extracted teeth after a 10 s application of ozone during the treatment of root carious lesions were as shown in Table 3.

TABLE 3

Maximum ozone detectable level (ppm)

| Teeth types | Sites | Ozone detection |
| --- | --- | --- |
| Upper incisor | Mesial | 0.005 |
| Upper lateral incisor | Labial | 0.004 |
| Upper canine | Labial | 0.003 |
| Upper 1. premolar | Mesial | 0.006 |
| Upper 2. premolar | Distal | 0.002 |
| Upper 1. molar | Buccal | 0.003 |
| Upper 2. molar | Mesial | 0 |
| Lower incisor | Lingual | 0.007 |
| Lower lateral incisor | Distal | 0.001 |
| Lower canine | Mesial | 0 |
| Lower 1. premolar | Distal | 0.009 |
| Lower 2. premolar | Lingual | 0.018 |
| Lower 1. molar | Lingual | 0.016 |
| Lower 2. molar | Mesial | 0.005 |

Conclusion: The use of a cup is a safe way of delivering ozone when ozone was applied for a period of 10 s on the root carious lesions on extracted teeth.

EXAMPLE 3

Measurement of Ozone from the Handpiece

The handpiece 16 from the ozone generator 20 was attached directly to the inlet pipe a Mini-HiCon™ the ozone detector (not shown).

| | Peak readings from Mini-HiCon ™ (g/Nm³) | | | | | | |
|---|---|---|---|---|---|---|---|
| Duration (seconds) | Reading 1 (g/Nm³) | Reading 2 (g/Nm³) | Reading 3 (g/Nm³) | Reading 4 (g/Nm³) | Reading 5 (g/Nm³) | Reading 6 (g/Nm³) | Average (g/Nm³) |
| 5 | 5.4 | 5.3 | 5.4 | 4.3 | 5.2 | 5.2 | 5.1 |
| 10 | 4.7 | 4.8 | 4.6 | 3.5 | 4.4 | 4.5 | 4.4 |
| 20 | 4.9 | 5.9 | 6.3 | 6.3 | | | 5.9 |
| 30 | 6.3 | 6.5 | 6.3 | 6.6 | | | 6.4 |
| 60 | 6.6 | 7.0 | 7.0 | 6.7 | | | 6.8 |

| | Peak readings from Mini-HiCon ™ (ppm) | | | | | | |
|---|---|---|---|---|---|---|---|
| Duration (seconds) | Reading 1 (ppm) | Reading 2 (ppm) | Reading 3 (ppm) | Reading 4 (ppm) | Reading 5 (ppm) | Reading 6 (ppm) | Average (ppm) |
| 5 | 2522 | 2475 | 2522 | 2008 | 2428 | 2428 | 2397 |
| 10 | 2195 | 2242 | 2148 | 1635 | 2055 | 2102 | 2063 |
| 20 | 2288 | 2755 | 2942 | 2942 | | | 2732 |
| 30 | 2942 | 3036 | 2942 | 3082 | | | 3000 |
| 60 | 3082 | 3269 | 3269 | 3129 | | | 3187 |

The peak reading was obtained after about 8 seconds (even when the generator was switched on for only 5 seconds) and perhaps represented an "overshoot" before the generator/detector combination stabilized for the >20 second durations. The level then remained fairly constant at between 3.6 and 4.7 g/Nm³.

To Convert From g/m³ to ppm:

The formula weight of ozone is 48 g and therefore 1 g of ozone is ¹/₄₈th of a mole.

The molar volume of an ideal gas (at standard temperature and pressure) is 0.0224138 m³/mol.

$0.0224138/48 = 467 \times 10^{-6}$ m³.

Therefore 1 g/m³ of ozone in air is 467 ppm.

(The ozone detector gives readings as g/Nm³ which is "normalized" to standard temperature and pressure).

Measurement of the Ozone Dissolving in a Potassium Iodide Solution

Ozone was passed through the handpiece 16, immersed in 100 ml of a 20 mM potassium iodide solution in a 250 ml conical flask covered with parafilm for the stated durations. The handpiece was then removed and the flask sealed with a neoprene bung and shaken vigorously. A 1.50 ml aliquot was removed and its electronic absorption spectrum acquired. (These measurements were taken before a diffuser was fitted.) The generator settings were:—air=1, O₃=1, vac=0, red=0, regulator-setting=10.

| Duration (seconds) | $\lambda_{max}$ (351 nm) absorbance | $\lambda_{max}$ (351 nm) absorbance | $\lambda_{max}$ (351 nm) absorbance | $\lambda_{max}$ (351 nm) average absorbance |
|---|---|---|---|---|
| 1 | 0.06 | 0.08 | 0.11 | 0.08 |
| 2 | 0.50 | 0.44 | 0.26 | 0.40 |
| 3 | 0.70 | 0.56 | 0.42 | 0.56 |

-continued

| Duration (seconds) | $\lambda_{max}$ (351 nm) absorbance | $\lambda_{max}$ (351 nm) absorbance | $\lambda_{max}$ (351 nm) absorbance | $\lambda_{max}$ (351 nm) average absorbance |
|---|---|---|---|---|
| 4 | 0.77 | 0.69 | 0.50 | 0.65 |
| 5 | 0.90 | 0.84 | 0.51 | 0.75 |
| 6 | 1.08 | 0.99 | 0.68 | 0.92 |
| 7 | 1.17 | 1.11 | 0.75 | 1.01 |
| 8 | 1.30 | 1.27 | 0.95 | 1.17 |
| 9 | 1.40 | 1.40 | 1.19 | 1.33 |
| 10 | 1.57 | 1.43 | 1.38 | 1.46 |

To Calculate the Concentration from the Peak Absorbance:

$A = E \times C \times L$ where
L = cell path length (1 cm)
C = concentration (mol)
E = extinction coefficient
A = absorbance E for 1 M = $2.97 \times 10^4$
E for 1 μM = 0.0297
$C = A \div E \Rightarrow$ concentration in μmol/l is absorbance/0.0297

| Duration (seconds) | $\lambda_{max}$ absorbance (average of 3) | Concentration (µmol/l) | Total dissolved ozone (µmol) | Ozone (µg) | Volume of air/ozone mixture (ml) | Ozone in air (µg/ml = g/m³) | Ozone in air (ppm) |
|---|---|---|---|---|---|---|---|
| 1 | 0.08 | 2.69 | 0.269 | 13 | 8 | 1.625 | 759 |
| 2 | 0.40 | 13.47 | 1.347 | 65 | 16 | 4.063 | 1897 |
| 3 | 0.50 | 18.86 | 1.886 | 91 | 24 | 3.792 | 1771 |
| 4 | 0.65 | 21.89 | 2.189 | 105 | 32 | 3.281 | 1532 |
| 5 | 0.75 | 25.25 | 2.525 | 121 | 40 | 3.025 | 1413 |
| 6 | 0.92 | 30.98 | 3.098 | 149 | 48 | 3.104 | 1450 |
| 7 | 1.01 | 34.39 | 3.439 | 165 | 56 | 2.946 | 1376 |
| 8 | 1.17 | 39.39 | 3.939 | 189 | 64 | 2.953 | 1379 |
| 9 | 1.33 | 44.79 | 4.479 | 215 | 72 | 2.986 | 1394 |
| 10 | 1.46 | 49.16 | 4.916 | 236 | 80 | 2.950 | 1378 |

NMR Analysis of Plaque/Caries
1. Plaque samples were obtained from volunteers and each sample was divided into two. Half of each sample was treated with ozone and half left untreated as a control.
2. The samples were each weighed. Then 600 µl of 0.5 M $HClO_4$ was added to each sample and rotamixed.
3. The samples were centrifuged and supernatants retained.
4. The samples were neutralized to a pH of between 6 and 8 and the volume of KOH used was noted.
5. The samples were centrifuged again and 600 µl of supernatant were taken for analysis.
6. 70 µl of $D_2O$ and 30 µl of sodium 3-trimethylsilyl-(2,2,3,3,-²H₄)-propionate (5 mM in $D_2O$) were added prior to NMR analysis.

NMR Analysis of Saliva
1. Saliva samples were obtained from volunteers and each sample was divided into two. Half of each sample was treated with ozone and half left untreated as a control.
2. The samples were centrifuged and supernatants retained.
3. 70 µl of $D_2O$ and 30 µl of sodium 3-trimethylsilyl-(2,2,3,3, -²H₄)-propionate (5 mM in $D_2O$) were added prior to NMR analysis.

Iodine Standards (in 20 mM Potassium Iodide)

| Iodine Concentration | Absorbance at 351 nm |
|---|---|
| 4 uM | 0.1144 |
| 5 uM | 0.1410 |
| 7 uM | 0.1690 |
| 10 uM | 0.2002 |

Although there has been hereinabove described method apparatus for the treatment of dental and oral condition in accordance with the present invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the invention as defined in the appended claims.

What is claimed is:

1. A method of treating mouth ulcerations, said method comprising:
    directing an ozone onto a mouth ulceration;
    maintaining a presence of the ozone gas onto the mouth ulceration for a period of time sufficient to kill microorganisms therein; and
    preventing escape of the ozone gas from the mouth ulceration.

2. A method of treating mouth ulcerations, said method comprising:
    directing ozone gas onto a mouth ulceration;
    maintaining a presence of the ozone gas onto the mouth ulceration for a period of time sufficient to kill microorganisms therein;
    preventing escape of the ozone gas from the mouth ulceration; and
    flushing the ozone gas from the mouth ulceration with a reductant.

* * * * *